(12) United States Patent
Ernst et al.

(10) Patent No.: US 8,884,063 B2
(45) Date of Patent: Nov. 11, 2014

(54) CONTINUOUS PROCESS FOR THE HYDROGENATION OF 3-CYANO-3,5,5-TRIMETHYL-CYCLOHEXYLIMINE

(75) Inventors: Martin Ernst, Heidelberg (DE); Thomas Hill, Ludwigshafen (DE); Piotr Makarczyk, Ludwigshafen (DE); Johann-Peter Melder, Böhl-Iggelheim (DE)

(73) Assignee: BASF SE (DE)

( * ) Notice: Subject to any disclaimer, the term of this patent is extended or adjusted under 35 U.S.C. 154(b) by 1237 days.

(21) Appl. No.: 12/520,575

(22) PCT Filed: Dec. 19, 2007

(86) PCT No.: PCT/EP2007/064171
§ 371 (c)(1),
(2), (4) Date: Jun. 22, 2009

(87) PCT Pub. No.: WO2008/077852
PCT Pub. Date: Jul. 3, 2008

(65) Prior Publication Data
US 2010/0036168 A1  Feb. 11, 2010

(30) Foreign Application Priority Data
Dec. 22, 2006 (EP) .................................. 06127089

(51) Int. Cl.
C07C 209/00 (2006.01)
C07C 209/52 (2006.01)
C07C 209/48 (2006.01)

(52) U.S. Cl.
CPC ............. *C07C 209/48* (2013.01); *C07C 209/52* (2013.01); *C07C 2101/14* (2013.01)
USPC ........................................................ 564/448

(58) Field of Classification Search
None
See application file for complete search history.

(56) References Cited

U.S. PATENT DOCUMENTS

| | | |
|---|---|---|
| 5,371,292 A | 12/1994 | Merger et al. |
| 5,504,254 A | 4/1996 | Haas et al. |
| 5,756,845 A | 5/1998 | Voit et al. |
| 6,011,179 A | 1/2000 | Haas et al. |
| 6,022,999 A | 2/2000 | Voit et al. |

FOREIGN PATENT DOCUMENTS

| | | |
|---|---|---|
| DE | 4010227 A1 | 10/1991 |
| DE | 4343890 A1 | 6/1995 |
| DE | 19507398 C1 | 9/1996 |
| DE | 19747913 C1 | 2/1999 |
| DE | 19756400 A1 | 6/1999 |
| EP | 0394968 A1 | 10/1990 |
| EP | 0449089 A1 | 10/1991 |
| EP | 0623585 A1 | 11/1994 |

*Primary Examiner* — Clinton Brooks
(74) *Attorney, Agent, or Firm* — Drinker Biddle & Reath LLP

(57) ABSTRACT

The present invention relates to a continuous process for preparing 3-aminomethyl-3,5,5-trimethylcyclohexylamine by reacting a feed stream comprising 3-cyano-3,5,5-trimethylcyclohexylimine with hydrogen and ammonia over hydrogenation catalysts, wherein the basicity of the reaction mixture is increased during the reaction by bringing the reaction mixture into contact with a basic compound which is not ammonia and/or a basic catalyst after part of the 3-cyano-3,5,5-trimethylcyclohexylimine has been reacted.

17 Claims, No Drawings

CONTINUOUS PROCESS FOR THE HYDROGENATION OF 3-CYANO-3,5,5-TRIMETHYL-CYCLOHEXYLIMINE

CROSS-REFERENCE TO RELATED APPLICATIONS

This application is a national stage application (under 35 U.S.C. §371) of PCT/EP2007/064171, filed Dec. 19, 2007, which claims benefit of European application 06127089.8, filed Dec. 22, 2006.

BACKGROUND OF THE INVENTION

The present invention relates to a continuous process for preparing 3-aminomethyl-3,5,5-trimethylcyclohexylamine by reacting a feed stream comprising 3-cyano-3,5,5-trimethylcyclohexylimine with hydrogen and ammonia over hydrogenation catalysts.

3-Aminomethyl-3,5,5-trimethylcyclohexylamine (isophoronediamine, IPDA) is an important intermediate for polyamides and epoxy resins and for preparing the downstream product isophorone diisocyanate (IPDI) which is used as a component in polyurethanes.

On an industrial scale, 3-aminomethyl-3,5,5-trimethylcyclohexylamine is prepared by reacting 3-cyano-3,5,5-trimethylcyclohexanone (isophorone nitrile, IPN) with ammonia to form 3-cyano-3,5,5-trimethylcyclohexylimine (isophorone nitrile imine, IPNI).

IPNI is subsequently reacted catalytically with hydrogen in the presence of ammonia in a reductive amination reaction to form 3-cyano-3,5,5-trimethylcyclohexylamine (isophoronediamine, IPDA).

The reductive amination can be carried out in a plurality of stages to increase the yield. Thus, EP-A1-0394968 describes a multistage process in which the imino group of IPNI is firstly selectively hydrogenated and the hydrogenation of the nitrile group is subsequently effected under more drastic reaction conditions (higher pressure and temperature). According to the disclosure, the formation of 3-cyano-3,5,5-trimethylcyclohexanol, which is formed by reduction of the 3-cyano-3,5,5-trimethylcyclohexanone which is in equilibrium with IPNI, can be reduced by carrying out the reaction in this way. However, the proportion of further by-products, e.g. cyclic compounds, is from 3 to 7% in the examples.

Good yields are achieved when the reductive amination is carried out in the presence of basic catalysts or compounds. Thus, in DE-A-4010227, the reductive amination is partly carried out in the presence of basic catalysts, and good yields are achieved.

In EP-A1-0623585, it is shown that doping of catalysts with basic components leads to higher yields in the reductive amination.

DE-C-19747913 describes a process for hydrogenating imines and nitriles to form amines, in particular IPDA, with the yield being increased by addition of a quaternary ammonium hydroxide.

In the preparation of IPDA, it is very important not only to achieve a high product yield but to control the isomer ratio between cis-isophoronediamine and trans-isophoronediamine in the reductive amination, since the isomers have different reactivities. Thus, the cis/trans ratio influences the further processing of IPDA and its downstream product IPDI and therefore also the product properties of the products produced from these raw materials. Commercial IPDI generally has a cis/trans ratio (CTR) of from 74:26 to 78:22.

Such an isomer ratio can be set by means of the process described in EP-A1-0394968. The hydrogenation of isophorone nitrile (IPN) is carried out in a temperature range from 10 to 90° C. in a first reaction stage and subsequently at from 90 to 160° C. in the second reaction stage, with the temperature difference between the first and second reaction stages being at least 30° C. and the residence time in the first reaction stage being shorter than in the second reaction stage. Variation of the temperature of the first reaction stage enabled a CTR of from 55.45 to 80:20 to be set, with the yield going through a maximum at a CTR of 76:24.

According to DE-C-19507398, the amount of base used in the hydrogenative amination also has an influence on the isomer ratio. Thus, an increase in the CTR from 60:40 to 68:32 was able to be achieved by decreasing the concentration of base. However, the reduction in the concentration of base also led to a decrease in the yield from 97 to about 92%.

A further increase in the CTR to 75:25 was able to be achieved in DE-A-19756400 when the reductive amination was carried out in the presence of an acid. The yields were in the region of 92%.

The catalyst used in the reductive amination can also influence the isomer ratio. Thus, DE-A-4343890 reports that the CTR is increased by the use of ruthenium rather than cobalt or cobalt-comprising catalysts, but the yield decreases.

The present invention provides a process which makes it possible to increase the isomer ratio at an at least constant or improved yield and to achieve high space-time yields. In particular, the formation of by-products which are difficult to separate off from the reaction mixture should be prevented by means of this process. Furthermore, the process economics should be increased by means of an improved yield.

DETAILED DESCRIPTION OF THE INVENTION

We have accordingly found a continuous process for preparing 3-aminomethyl-3,5,5-trimethyl-cyclohexylamine by reacting a feed stream comprising 3-cyano-3,5,5-trimethyl-cyclohexylimine with hydrogen and ammonia over hydrogenation catalysts, wherein the basicity of the reaction mixture is increased during the reaction by bringing the reaction mixture into contact with a basic compound which is not ammonia and/or a basic catalyst after part of the 3-cyano-3,5,5-trimethylcyclohexylimine has been reacted.

The 3-cyano-3,5,5-trimethylcyclohexylimine-comprising feed stream is generally obtained by reacting 3-cyano-3,5,5-trimethylcyclohexanone (IPN) with excess ammonia in the presence of an imine formation catalyst (imination).

Possible imine formation catalysts are, for example, solid Brönsted or Lewis acids as are described, for example, in EP-A1-449089 (page 2, column 2, lines 11-20) and in the article by Tanabe et al. (K. Tanabe, Studies in Surface Science and Catalysis, Vol. 51, 1989, p. 1 ff). For example, mention is here made of acidic metal oxide catalysts such as aluminum oxide, titanium dioxide, zirconium dioxide and silicon dioxide. It is also possible to use inorganic or organic ion exchangers such as zeolites or sulfonated copolymers of styrene and divinylbenzene (e.g. the Lewatit® grades from Lanxess, Amberlite® from Rohm & Haas) or ion exchangers based on siloxane (e.g. Deloxan® from Degussa) laden with ammonium ions.

It is usual to use from 5 to 500 mole of ammonia ($NH_3$), preferably from 10 to 400 mole of $NH_3$, particularly preferably from 20 to 300 mole of $NH_3$, per mole of IPN used.

The imination of IPN can be carried out in the presence of a solvent, for example in alkanols or ethers, e.g. ethanol, butanol or tetrahydrofuran (THF). The imination of IPN is preferably carried out without addition of solvents.

The imination is preferably carried out continuously, usually in pressure vessels or cascades of pressure vessels. Preference is given to passing IPN and NH$_3$ through a tube reactor in which the imine formation catalyst is present in the form of a fixed bed.

The imination is preferably carried out in the temperature range from 20 to 150° C., preferably from 30 to 130° C. and particularly preferably from 50 to 100° C.

The pressure in the imination is generally from 50 to 300 bar, preferably from 100 to 250 bar.

In general, a space velocity over the catalyst of from 0.01 to 10, preferably from 0.05 to 7, particularly preferably from 0.1 to 5, kg of IPN per kg of catalyst and hour is set during the imination.

The output from the imination reaction usually comprises IPNI and ammonia and unreacted IPN. The conversion of IPN into IPNI is usually more than 80%, preferably more than 90% and particularly preferably more than 95%.

The output from the imination reaction is reacted as 3-cyano-3,5,5-trimethylcyclohexylimine-comprising feed stream with hydrogen and ammonia over hydrogenation catalysts (reductive amination).

BRIEF SUMMARY OF THE INVENTION

The invention relates to a continuous process for preparing 3-aminomethyl-3,5,5-trimethylcyclohexylamine which comprises reacting a feed stream comprising 3-cyano-3,5,5-trimethylcyclohexylimine with hydrogen and ammonia over hydrogenation catalysts, wherein the basicity of the reaction mixture is increased during the reaction by bringing the reaction mixture into contact with a basic compound which is not ammonia and/or a basic catalyst after part of the 3-cyano-3,5,5-trimethylcyclohexylimine has been reacted.

The reaction of the feed stream comprising 3-cyano-3,5,5-trimethylcyclohexylimine is preferably carried out in liquid ammonia. It is usual to use from 5 to 500 mole of NH$_3$, preferably from 10 to 400 mole of NH$_3$ and particularly preferably from 20 to 300 mole of NH$_3$, per mole of IPNI (3-cyano-3,5,5-trimethylcyclohexylimine). It is advantageous to set the molar ratio of IPN to NH$_3$ in the preceding imination so that the molar ratio is also in a suitable range in the reductive amination. However, the proportion of NH$_3$ can be increased to a desired value by addition of additional NH$_3$ before the reductive amination.

Hydrogen is used as further starting material for the reaction of the 3-cyano-3,5,5-trimethylcyclohexylimine-comprising feed stream. The molar ratio of hydrogen to IPNI is generally 3-10 000:1, preferably 4-5000:1 and particularly preferably 5-1000:1.

The hydrogen is preferably added to the 3-cyano-3,5,5-trimethylcyclohexylimine-comprising feed stream after the imination and before the reductive amination. However, it is also conceivable for the hydrogen to be introduced before the imination since the imination is usually carried out over catalysts which do not catalyze the hydrogenation. Thus, the hydrogen introduced prior to the imination can also be available as starting material for the reaction of the 3-cyano-3,5,5-trimethyl-cyclohexylimine-comprising feed stream during the reductive amination.

As hydrogenation catalysts, it is in principle possible to use all hydrogenation catalysts which comprise nickel, cobalt, iron, copper, ruthenium and/or other metals of transition group VIII of the Periodic Table. Further suitable hydrogenation catalysts are catalysts comprising the elements chromium, manganese, copper, molybdenum, tungsten and/or rhenium.

Preference is given to using hydrogenation catalysts comprising ruthenium, cobalt and/or nickel. Particular preference is given to catalysts comprising ruthenium and/or cobalt.

The abovementioned hydrogenation catalysts can be doped in a customary fashion with promoters, for example chromium, iron, cobalt, manganese, thallium, molybdenum, titanium and/or phosphorus.

The catalytically active metals can be used as all-active catalysts or on supports. Possible supports for this purpose, are, for example, aluminum oxide, titanium dioxide, zirconium dioxide or magnesium oxide/aluminum oxide. The supports can also be imination-active to make reaction of the ketone present in equilibrium with the imine during the hydrogenation of the imine group possible.

The catalytically active metals can also be used in the form of sponge catalysts, known as Raney catalysts. As Raney catalysts, preference is given to using Raney cobalt catalysts, Raney nickel catalysts and/or Raney copper catalysts. Particular preference is given to using Raney cobalt catalysts.

Selective hydrogenation catalysts can also be advantageously used as hydrogenation catalysts. For the present purposes, selective hydrogenation catalysts are catalysts which preferentially hydrogenate the imine group over the nitrite group of the 3-cyano-3,5,5-trimethylcyclohexylimine.

Selective hydrogenation catalysts are, for example, hydrogenation catalysts comprising ruthenium, palladium and/or rhodium. Preferred selective hydrogenation catalysts comprise ruthenium and/or rhodium and particularly preferred hydrogenation catalysts comprise ruthenium.

The reductive amination is preferably carried out continuously in pressure vessels. A tube reactor having a fixed catalyst bed is particularly useful for this reaction.

The space-velocity over the catalyst in continuous operation is typically from 0.01 to 10, preferably from 0.05 to 7, particularly preferably from 0.1 to 5, kg of IPNI per kg of catalyst and hour.

According to the invention, the basicity of the reaction mixture is increased during the reaction by bringing the reaction mixture into contact with a basic compound which is not ammonia and/or a basic catalyst after part of the 3-cyano-3,5,5-trimethylcyclohexylimine has been reacted.

The basicity of the reaction mixture comprising 3-cyano-3,5,5-trimethylcyclohexylimine, ammonia, hydrogen and the hydrogenation catalyst can be increased by bringing the reaction mixture into contact with a basic compound.

Here, it goes without saying that the term basic compound does not encompass the starting material ammonia but instead comprises one or more of the compounds mentioned below or compounds which act in an analogous fashion to the compounds mentioned below.

Thus, the basicity of the reaction mixture can be increased by adding a basic compound to the reaction mixture.

In a further embodiment, the basicity of the reaction mixture can be increased by bringing a basic hydrogenation catalyst into contact with the reaction mixture.

Suitable basic compounds include basic metal compounds such as the oxides, hydroxides or carbonates of the alkali, alkaline earth or rare earth metals.

Preference is given to the metal compounds of the alkali and alkaline earth metals, for example the corresponding oxides, hydroxides and carbonates, e.g. Li$_2$O, Na$_2$O, K$_2$O, Rb$_2$O, Cs$_2$O, LiOH, NaOH, KOH, RbOH, CsOH, Li$_2$CO$_3$, Na$_2$CO$_3$, K$_2$CO$_3$, Cs$_2$CO$_3$, Rb$_2$CO$_3$, MgO, CaO, SrO, BaO, Mg(OH)$_2$, Ca(OH)$_2$, Sr(OH)$_2$, Ba(OH)$_2$, MgCO$_3$, CaCO$_3$, SrCO$_3$ or BaCO$_3$. Particular preference is given to LiOH, NaOH or KOH.

Further preferred basic compounds are amines or ammonium hydroxides.

Particular preference is given to adding solutions of the basic compounds in water or other suitable solvents, for example alkanols such as C$_1$-C$_4$-alkanols, e.g. methanol or ethanol, or ethers such as cyclic ethers, e.g. THF or dioxane, to the reaction mixture. Particular preference is given to adding solutions of alkali metal or alkaline earth metal hydroxides in water particularly preferably solutions of LiOH, NaOH or KOH in water.

The concentration of the basic compound in water or other suitable solvents is preferably from 0.01 to 20% by weight, preferably from 0.1 to 10% by weight and particularly preferably from 0.2 to 5% by weight.

The amount of the solution of the basic compound added is usually selected so that the ratio of the mass of the basic compound added to the mass of the 3-cyano-3,5,5-trimethylcyclohexylimine in the feed stream is 100-10 000:1 000 000, preferably 150-5000:1 000 000 and particularly preferably 200-1 000 000.

For the purposes of the present invention, the basicity can also be increased by using basic hydrogenation catalysts. Such basic hydrogenation catalysts are hydrogenation catalysts as mentioned above which have been doped with basic components such as oxides or hydroxides of alkali, alkaline earth and rare earth metals and/or been applied to basic supports.

Suitable basic supports for hydrogenation catalysts are, for example, β-aluminum oxide or magnesium oxide/aluminum oxide mixtures, with the proportion of magnesium oxide preferably being from 5 to 40% by weight. Here, the support comprising magnesium oxide and aluminum oxide can be amorphous or be present as spinel. Catalysts on basic supports are obtained industrially in a manner known per se. Thus, for example, ruthenium on basic supports is obtained by applying aqueous ruthenium salt solutions such as ruthenium chloride and ruthenium nitrate to the appropriate basic support.

The concentration of the metals, in particular ruthenium, on the basic supports is generally from 0.1 to 10% by weight, preferably from 0.5 to 5% by weight and particularly from 1 to 4% by weight.

Basic catalysts also include hydrogenation catalysts which have been doped with the abovementioned basic components, e.g. oxides or hydroxides of alkali, alkaline earth and rare earth metals. Basic catalysts preferably comprise at least one basic component such as Li$_2$O, Na$_2$O, K$_2$O, MgO, CaO, SrO or BaO.

The proportion of basic components, i.e. basic dopants, in basic hydrogenation catalysts is generally more than 0.5% by weight and particularly preferably more than 0.7% by weight and more particularly preferably more than 1% by weight, based on the total mass of the basic hydrogenation catalyst.

The hydrogenation catalysts described at the outset which have not been applied to basic supports as described above and/or comprise 0.5% by weight or less of basic components, i.e. basic dopants, based on the total mass of the catalyst, will hereinafter be referred to as nonbasic hydrogenation catalysts.

According to the invention, the basicity of the reaction mixture is increased during the reaction by bringing the reaction mixture into contact with a basic compound after part of the 3-cyano-3,5,5-trimethylcyclohexylimine has been reacted.

In general, the basicity is increased by bringing the reaction mixture into contact with the basic compound after from 1 to 95%, preferably from 5 to 80% and particularly preferably from 10 to 40%, of the 3-cyano-3,5,5-trimethylcyclohexylimine in the feed stream has been reacted.

In general, no basic compounds are added to the reaction mixture before the basicity is increased. However, it is possible for the reaction mixture to comprise small amounts of basic compounds. However, the ratio of the mass of the basic compound to the mass of the 3-cyano-3,5,5-trimethylcyclohexylimine in the feed stream is preferably less than 100:1 000 000, preferably less than 50:1 000 000, before the basicity is increased.

Before the basicity is increased, the reaction mixture is usually brought into contact with nonbasic catalysts.

The reductive amination, i.e. the reaction of the 3-cyano-3,5,5-trimethylcyclohexylimine-comprising feed stream with hydrogen and ammonia over hydrogenation catalysts, can be carried out in one reaction space or in a plurality of separate reaction spaces.

If the reductive amination is carried out in only one reaction space, for example in a fixed-bed reactor, the contacting of the reaction mixture with the basic compound to increase the basicity can be effected by introducing the basic compound between the reactor inlet into which the 3-cyano-3,5, 5-trimethylcyclohexylimine-comprising feed stream together with ammonia and hydrogen is fed and the reactor outlet. According to the invention, the contacting of the feed stream with the basic compound cannot be carried out before the reductive amination.

Since the reaction is, as described above, preferably carried under a high pressure, it is necessary for the introduction of the basic compound to be effected at a high operating pressure in the reactor. Suitable technical apparatuses for introducing substances under high-pressure conditions are known to those skilled in the art. In particular, it is possible to use pumps such as high-pressure pumps or piston pumps for introducing substances under high-pressure conditions.

However, it is also possible for the contacting of the reaction mixture with a basic catalyst to increase the basicity of the reaction mixture to be effected by firstly passing the 3-cyano-3,5,5-trimethylcyclohexylimine-comprising feed stream together with hydrogen and ammonia over one of the above-described nonbasic hydrogenation catalysts and subsequently over a basic hydrogenation catalyst. This can be achieved by the catalysts being present in appropriate zones.

A basic compound is, as described above, advantageously introduced at the transition between the zone of the nonbasic hydrogenation catalyst and the basic hydrogenation catalyst since the basic components of the hydrogenation catalyst can be washed out as the period of operation increases.

The reductive amination is carried out at temperatures of from 50 to 160° C. and a pressure of from 50 to 300 bar.

The temperature profile between reactor inlet and reactor outlet is usually largely constant and determined by the heat of reaction liberated in the reductive amination. However, it is also possible to set a temperature profile between reactor inlet and reactor outlet. Such a temperature profile can be established by individual regions of the reactor being able to be heated separately to degrees which can be individually set. In such a case, it is advantageous for the temperature to be increased from the reactor inlet to the reactor outlet. The temperature at the reactor inlet is preferably in the range from 50 to 100° C., while the temperature at the reactor outlet is preferably from 100 to 160° C. The increasing temperature profile from reactor inlet to reactor outlet can be a continuous function or can have discrete steps.

In a preferred embodiment, however, the reductive amination is carried out in two or more stages, with the stages being carried out in separate reaction spaces.

In a particularly preferred embodiment, the reductive amination is carried out in two stages, with the stages being carried out in separate reaction spaces.

The first stage (stage I) is generally carried out in a temperature range from 50 to 100° C., preferably from 55 to 95° C. and particularly preferably from 60 to 90° C., and at a pressure of from 15 to 300 bar, preferably from 20 to 250 bar and particularly preferably from 30 to 230 bar.

The second stage (stage II) is usually carried out in a temperature range from 70 to 160° C., preferably from 75 to 150° C. and particularly preferably from 80 to 140° C., and at a pressure of from 50 to 300 bar, preferably from 80 to 250 bar and particularly preferably from 100 to 230 bar.

Both stages are usually carried out in pressure vessels, in particular in fixed-bed reactors.

As catalysts, it is possible to use the above-described nonbasic hydrogenation catalysts in both stages, with preference being given to using a nonbasic catalyst comprising cobalt.

In a preferred embodiment, the above-described selective hydrogenation catalysts are used as nonbasic hydrogenation catalysts in stage I.

The contacting of the reaction mixture with the basic compound to increase the basicity of the reaction mixture is, in the above-described embodiments, preferably effected by introducing a solution of a basic compound between the outlet from stage I and the inlet into stage II.

However, the contacting of the reaction mixture with a basic compound to increase the basicity of the reaction mixture can also be effected by using one of the above-described nonbasic hydrogenation catalysts in stage I and a basic hydrogenation catalyst in stage II.

Since the basic components can be washed out of the basic catalyst as the period of operation increases, it is advantageous for a solution of a basic compound to be additionally introduced between the outlet from stage I and the inlet into stage II.

In further embodiments of the invention, it is possible to subdivide both stage I and stage II into further substages, with the substages also being able to be carried out in separated reaction spaces.

It is thus possible to carry out the substages of stage I in two or more pressure vessels, in particular fixed-bed reactors.

As described above, the substages of stage I are usually carried out in a temperature range from 50 to 100° C. and a pressure from 15 to 300 bar. Pressure and temperature can be identical or different in the substages. The substages are advantageously operated at the same temperature and the same pressure. If the substages are operated at different temperatures and pressures, it is advantageous for pressure and temperature to increase from substage to substage, i.e. for the pressure and the temperature to be lowest in the first substage.

The above-described nonbasic hydrogenation catalysts can be used in each substage.

In a preferred embodiment, selective hydrogenation catalysts are used as nonbasic hydrogenation catalysts in the first substage or in the first substages of the first reaction stage.

For reasons of process economics, it is advantageous for stage I of the reductive amination to comprise not more than three substages, preferably two substages and particularly preferably one substage, since the capital cost increases with increasing number of reactors.

If stage I of the reductive amination is carried out in only one substage, it is advantageous for the basicity of the reaction mixture to be increased by bringing the reaction mixture into contact with the basic compound downstream of the outlet from stage I.

If stage I of the reductive amination is carried out in two or more substages, it is advisable to increase the basicity of the reaction mixture by bringing the reaction mixture into contact with the basic compound downstream of the first substage of stage I.

The reaction mixture is preferably brought into contact with the basic compound by introducing the basic compound between the outlet from one substage and the inlet into the next substage of stage I.

The basic compound is advantageously introduced between the first substage and the second substage of stage I. However it is also possible to introduce the basic compound between the outlet and the inlet of any two successive substages. However, according to the invention, the introduction of the basic compound must not be effected before the first substage of stage I.

The contacting of the reaction mixture with a basic hydrogenation catalyst to increase the basicity of the reaction mixture can also be carried out by using one of the above-described nonbasic hydrogenation catalysts in the first substage or first substages and using a basic hydrogenation catalyst in one of the subsequent substages. It is also conceivable for zones of nonbasic hydrogenation catalysts and basic hydrogenation catalysts to be present in the substages.

Furthermore, it is advantageous for a solution of a basic compound to be additionally introduced into the substages having basic hydrogenation catalysts in order to compensate for the possibility of the basic components of the basic hydrogenation catalyst being washed out.

It is also possible to subdivide stage II of the reductive amination into further substages, with the substages preferably being carried out in separate reaction spaces.

The substages of stage II of the reductive amination are, as described above, usually carried out in a temperature range from 70 to 160° C. and at a pressure in the range from 50 to 300 bar. The substages of stage II of the reductive amination are preferably carried out in two or more pressure vessels, in particular fixed-bed reactors.

The contacting of the reaction mixture with a basic compound and/or a basic hydrogenation catalyst to increase the basicity of the reaction mixture should preferably be carried out upstream of stage II. However, it is also possible to carry out the contacting of the reaction mixture in one of the substages of the second reaction stage. This can be effected in an analogous fashion by introducing a solution of a basic compound between the substages of stage II or using a basic hydrogenation catalyst downstream of the first substage of stage II.

Furthermore, arrangement of hydrogenation catalysts and basic hydrogenation catalysts in zones in the substages of stage II is possible.

$NH_3$ and hydrogen are separated off, if appropriate under superatmospheric pressure, from the output obtained from the reductive amination reaction. The crude IPDA obtained in this way can, for example, be isolated by fractional rectification.

It is possible to regulate the CTR in the output from the reaction by dividing the 3-cyano-3,5,5-trimethylcyclohexylimine-comprising feed stream before introduction into stage I of the reductive amination. Part is fed together with hydrogen and $NH_3$ into stage I or into the first substage of stage I, while the other part is fed into a later stage (stage II) or substage of stage I or stage II. Preference is given to part of the 3-cyano-3,5,5-trimethylcyclohexylimine-comprising feed stream being fed into the second stage of the reductive amination (stage II) or into a substage of the second stage of the reductive amination.

In general, the CTR is decreased by the division of the feed stream, so that the CTR can be adjusted by regulation of the division of the feed stream.

A further possible way of controlling the CTR is to regulate the temperature in the first substage of stage I. In both cases, the conversion of the feed stream in the first substage of stage I is ultimately regulated. The higher the conversion in stage I or in the first substage of stage I, the higher the CTR in the product stream.

The invention described makes it possible to achieve a high IPDA yield at a high CTR. The process presented can be operated at a high space-time yield. The formation of interfering by-products is very largely avoided.

The invention is illustrated in the following examples.

EXAMPLES

Comparative Example 1

An apparatus comprising 5 reactors was used.

The conversion of IPN into IPNI (imination) was carried out in the first two reactors.

In reactors 3 to 5, the IPNI-comprising output from the imination reaction was converted into IPDA (reductive amination)

Imination:

The first two reactors were charged with γ-aluminum oxide (4 mm extrudates).

The temperature in the first and second reactors was in each case 70° C. 14 g/h of IPN and 62 g/h of $NH_3$ were fed into the first reactor. In addition, 45 standard l (standard liters) per hour of hydrogen were fed in at a pressure of 230 bar.

Reductive Amination:

The 3rd and 4th reactors were filled with a nonbasic, selective hydrogenation catalyst (0.5% by weight of Ru on a γ-aluminum oxide support (Degussa)). The 5th reactor was charged with a reduced Co catalyst (composition: $Mn_3O_4$: 5-6.2% by weight, $Na_2O$: 0-0.5% by weight, $H_3PO_4$: 2.8-3.8% by weight, balance Co+CoO).

The temperature in the 3rd reactor was 70° C. (first substage of stage I of the reductive amination). The temperature in the 4th reactor was 80° C. (second substage of stage I of the reductive amination). In the 5th reactor, the temperature was 120° C. (stage II of the reductive amination).

The IPNI-comprising output from the imination reaction was introduced into the inlet of the 3rd reactor (first substage of stage I).

The reaction output after 91 hours comprised ammonia and water together with, according to gas-chromatographic analysis, 89.7% of IPDA and 4.4% of 1,3,3-trimethyl-6-azabicyclo[3.2.1]octane (bicyclic compound) and also 3.2% of 1,3,3-trimethyl-6-azabicyclo[3.2.1]oct-7-ylidenamine (amidine) plus 0.3% of amino nitrile, corresponding to a selectivity of 90%. The isomer ratio of cis:trans-IPDA was 86/14.

Example 1

The example was carried out in a manner analogous to Comparative Example 1.

However, after a total running time of 91 hours, 0.009 g per minute of a 1% strength by weight aqueous solution of NaOH was introduced at the inlet of the 5th reactor (stage II). All other parameters remained the same as in Example 1. The reaction output after 146 hours comprised ammonia and water together with, according to gas-chromatographic analysis, 93.3% of IPDA, 1.5% of bicyclic compound and 2.6% of amidine plus 0.13% of amino nitrite, corresponding to a selectivity of 93.4%. The isomer ratio of cis:trans IPDA was 85/15.

Comparison of Comparative Example 1 with Example 1 shows that the selectivity was able to be increased from 90 to 93.4% at a virtually constant CTR by increasing the basicity of the reaction mixture between stage I and stage II.

Comparative Example 2

An apparatus comprising 5 reactors was used.

The conversion of IPN into IPNI (imination) was carried out in the first two reactors.

In reactors 3 to 5, the IPNI-comprising output from the imination reaction was converted into IPDA (reductive amination)

Imination:

The first two reactors were charged with γ-aluminum oxide (4 mm extrudates).

The temperature in the imination was 80° C.

54 g/h of IPN and 239 g/h of $NH_3$ were fed into the first reactor.

In addition, 81 standard l per hour of hydrogen were fed in at a pressure of 230 bar.

Reductive Amination:

The 3rd, 4th and 5th reactors were charged with a nonbasic hydrogenation catalyst, namely a reduced Co catalyst (composition: $Mn_3O_4$: 5-6.2% by weight, $Na_2O$: 0-0.5% by weight, $H_3PO_4$: 2.8-3.8% by weight, balance Co+CoO).

The temperature in the 3rd reactor was 80° C. (first substage of stage I of the reductive amination), the temperature in the 4th reactor was 90° C. (second substage of stage II of the reductive amination) and that in the 5th reactor was 125° C. (stage II of the reductive amination).

The IPNI-comprising output from the imination reaction was introduced into the 3rd reactor (first substage of stage I).

The reaction output after 820 hours comprised ammonia and water together with, according to gas-chromatographic analysis, 94.2% of IPDA and 0.8% of 1,3,3-trimethyl-6-azabicyclo[3.2.1]octane (bicyclic compound) and also 0.9% of 1,3,3-trimethyl-6-azabicyclo[3.2.1]oct-7-ylidenamine (amidine) plus 0.8% of amino nitrile, corresponding to a selectivity of 94.9%. The isomer ratio of cis:trans-IPDA was 72/28.

Example 2

Example 2 was carried out in a manner analogous to Comparative Example 2.

However, after 1000 h, 0.036 ml per minute of 2% strength by weight NaOH was additionally introduced at the inlet of the 4th reactor (second substage of stage I). The introduction of base was thus effected according to the invention between the first and second substages of stage I of the reductive amination. All other parameters remained the same. The reaction output after 1275 hours comprised ammonia and water together with, according to gas-chromatographic analysis, 95.8% of IPDA and 0.5% of 1,3,3-trimethyl-6-azabicyclo [3.2.1]octane (bicyclic compound) and also 0.3% of 1,3,3-trimethyl-6-azabicyclo[3.2.1]oct-7-ylidenamine (amidine) plus 0.6% of amino nitrile, corresponding to a selectivity of 96.4%. The isomer ratio of cis:trans IPDA was 72/28.

Comparison of Comparative Example 2 with Example 2 shows that the selectivity was able to be increased from 94.9 to 96.4% at a constant CTR by increasing the basicity of the reaction mixture by addition of an NaOH solution between stage I and stage II.

Comparative Example 2a

This experiment was carried out in a manner analogous to Example 2, but the introduction of base was moved from the inlet of the 4th reactor to the inlet of the 3rd reactor, i.e. the basic compound was added before stage I of the reductive amination. All other parameters remained the same. The reaction output after 1300 hours comprised ammonia and water together with, according to gas-chromatographic analysis, now 95.3% of IPDA and 0.7% of 1,3,3-trimethyl-6-azabicyclo[3.2.1]oct-7-ylidenamine (amidine) plus 0.07% of amino nitrile, corresponding to a selectivity of 95.4%. The isomer ratio of cis:trans-IPDA was 70/30.

If the NaOH solution is added to the reaction mixture before commencement of the reaction of the 3-cyano-3,5,5-trimethylcyclohexylimine, reduced selectivities and isomer ratios (CTR) compared to Example 2 are obtained.

Comparative Example 3

An apparatus comprising 5 reactors was used.
The conversion of IPN into IPNI (imination) was carried out in the first two reactors.
In reactors 3 to 5, the IPNI-comprising output from the imination reaction was converted into IPDA (reductive amination)
Imination:
The first two reactors were charged with γ-aluminum oxide (4 mm extrudates).
The temperature in the first and second reactors was 70° C.
17 g/h of IPN and 80 g/h of $NH_3$ were fed into the first reactor. In addition, 20 standard l/h of hydrogen were fed in at a pressure of 230 bar.
Reductive Amination:
The 3rd reactor was charged with the conventional, selective hydrogenation catalyst 2% of Ru/aluminum oxide (Degussa). The 4th and 5th reactors were charged with a reduced Co catalyst (composition: $Mn_3O_4$: 5-6.2% by weight, $Na_2O$: 0-0.5% by weight, $H_3PO_4$: 2.8-3.8% by weight, balance Co+CoO). The temperature in the 3rd reactor was 70° C. (first substage of stage I of the reductive amination). The temperature in the 4th reactor was 92° C. (second substage of stage I of the reductive amination). In the 5th reactor, the temperature was 135° C. (stage II of the reductive amination).
70% of the IPNI-comprising output from the imination reactor were fed into the inlet of the 3rd reactor (first substage of stage I).
The reaction output after 190 hours comprised ammonia and water together with, according to gas-chromatographic analysis, 94.6% of IPDA and 2.1% of 1,3,3-trimethyl-6-azabicyclo[3.2.1]octane (bicyclic compound) and also 0.7% of 1,3,3-trimethyl-6-aza-bicyclo[3.2.1]oct-7-ylidenamine (amidine) plus 0.2% of amino nitrile, corresponding to a selectivity of 95%. The isomer ratio of cis:trans IPDA was 78/22.

Example 3

The example was carried out in a manner analogous to Comparative Example 1.
However, after a total running time of 269 hours, 0.023 g per minute of a 0.25% strength by weight aqueous solution of NaOH was introduced at the inlet of the 4th reactor (stage II).

All other parameters remained the same as in Example 1. The reaction output after 509 hours comprised ammonia and water together with, according to gas-chromatographic analysis, 97.0% of IPDA, 0.87% of bicyclic compound and 0.25% of amidine plus 0.12% of amino nitrile, corresponding to a selectivity of 97.1%. The isomer ratio of cis:trans-IPDA was 75/25.

The cis:trans ratio was able to be increased to 77/23 at virtually the same selectivity (97.2%) by increasing the temperature in the 3rd reactor to 80° C. after 700 hours.

Comparative Example 4a

An apparatus comprising 4 reactors was used.
In the first reactor, the conversion of IPN into IPNI (imination) was carried out.
In reactors 2 to 4, the IPNI-comprising output from the imination was converted into IPDA (reactive amination)
Imination:
The first reactor was filled with titanium dioxide (1.5 mm extrudates).
The temperature in the reactor was 80° C.
35 g/h of IPN and 110 g/h of $NH_3$ were fed into the first reactor. In addition, 84 standard l/h of hydrogen were fed in at a pressure of 230 bar.
Reductive Amination:
The 2nd, 3rd and 4th reactors were charged with a reduced cocatalyst (composition: $Mn_3O_4$: 5-6.2% by weight, $Na_2O$: 0-0.5% by weight, $H_3PO_4$: 2.8-3.8% by weight, balance Co+CoO). The temperature in the 2nd reactor was 70° C. (first substage of stage I of the reductive amination). The temperature in the 3rd reactor was 90° C. (2nd substage of stage I of the reductive amination). In the 4th reactor, the temperature was 145° C. (stage II of the reductive amination). No base was introduced.
The reaction output after 1198 hours comprised ammonia and water together with, according to gas-chromatographic analysis, 97.0% of IPDA and 0.9% of 1,3,3-trimethyl-6-azabicyclo[3.2.1]octane (bicyclic compound) plus 0.3% of amino nitrile, corresponding to a selectivity of 97.3%. The isomer ratio of cis:trans IPDA was 71/29.

Comparative Example 4b

The example was carried out in a manner analogous to comparative example 4a.
However, after a running time of 1540 hours, 0.012 g per minute of a 1% strength by weight aqueous solution of NaOH was introduced at the inlet of the 2nd reactor (first substage of stage I). All other parameters remained the same as in comparative example 4a. The reaction output after 1708 hours comprised ammonia and water together with, according to gas-chromatographic analysis, 97.9% of IPDA and 0.1% of 1,3,3-trimethyl-6-azabicyclo[3.2.1]octane (bicyclic compound) plus 0.4% amino nitrile, corresponding to a selectivity of 98.4%. The isomer ratio of cis:trans-IPDA was 68/32.

Example 4

The example was carried out in a manner analogous to comparative example 4b.
After a running time of 1708 hours the introduction of base was moved from the inlet of the second reactor (first substage of stage I) to the inlet of the 3rd reactor (second substage of stage I). All other parameters remained the same as in comparative example 4b. The reaction output after 1949 hours comprised ammonia and water together with, according to gas-chromatographic analysis, 98.0% of IPDA and 0.1% of 1,3,3-trimethyl-6-azabicyclo[3.2.1]octane (bicyclic compound) plus 0.4% amino nitrile, corresponding to a selectivity of 98.4%. The isomer ratio of cis:trans-IPDA was 72/28.

The invention claimed is:

1. A continuous process for preparing 3-aminomethyl-3,5,5-trimethylcyclohexylamine which comprises reacting a feed stream comprising 3-cyano-3,5,5-trimethyl-cyclohexylimine with hydrogen and ammonia over hydrogenation catalysts, wherein the basicity of the reaction mixture is increased during the reaction by bringing the reaction mixture into contact with an exogenously added basic compound and/or a basic catalyst after part of the 3-cyano-3,5,5-trimethylcyclohexylimine has been reacted wherein the basic compound is not ammonia.

2. The process according to claim 1, wherein the ratio of the mass of the basic compound to the mass of the 3-cyano-3,5,5-trimethylcyclohexylimine in the feed stream is less than 100:1 000 000 before the basicity is increased.

3. The process according to claim 1, wherein a nonbasic hydrogenation catalyst is used before increasing the basicity.

4. The process according to claim 3, wherein the nonbasic catalyst is supported on nonbasic support materials and/or the proportion of basic components in the nonbasic hydrogenation catalyst is less than 0.5% by weight, based on the total mass of the catalyst.

5. The process according to claim 1, wherein the basicity of the reaction mixture is increased by adding a basic compound as solution.

6. The process according to claim 5, wherein the amount of the basic compound added as solution is selected so that the ratio of the mass of the basic compound added to the mass of the 3-cyano-3,5,5-trimethylcyclohexylimine in the feed stream is 100-10 000:1 000 000.

7. The process according to claim 1, wherein the basicity of the reaction mixture is increased by using a basic hydrogenation catalyst as basic compound.

8. The process according to claim 7, wherein the proportion of basic components in the basic hydrogenation catalyst is at least 0.5% by weight based on the total mass of the basic hydrogenation catalyst and/or the hydrogenation catalyst is supported on a basic support.

9. The process according claim 5, wherein the basic components in the hydrogenation catalyst are oxides or hydroxides of alkali or alkaline earth metals and/or basic support materials or the basic compound consists of oxides or hydroxides of the alkali or alkaline earth metals, amines and/or ammonium hydroxides.

10. The process according to claim 1, wherein the catalyst is a cobalt-comprising hydrogenation catalyst.

11. The process according to claim 1, wherein the reaction is carried out in two stages (stage I and stage II).

12. The process according to claim 11, wherein stage I is carried out in a temperature range from 50 to 100° C. and at a pressure of from 15 to 300 bar and stage II is carried out in a temperature range from 70 to 160° C. and at a pressure of from 50 to 300 bar.

13. The process according to claim 12, wherein a ruthenium- and/or rhodium-comprising catalyst is used in stage I.

14. The process according to at least claim 11, wherein the reaction mixture is brought into contact with the basic compound after stage I.

15. The process according to claim 11, wherein stage I and/or stage II are/is carried out in two or more substages, with the reaction mixture being brought into contact with the basic compound at the earliest after the first substage of stage I.

16. The process according to claim 11, wherein the feed stream is divided by introducing part of the feed stream into stage I and part of the feed stream directly into stage II.

17. The process according to claim 1, wherein the basicity is increased after from 5 to 80% of the 3-cyano-3,5,5-trimethyl-cyclohexylimine has been reacted.

* * * * *